(12) United States Patent
Hogan

(10) Patent No.: US 10,856,780 B2
(45) Date of Patent: Dec. 8, 2020

(54) SPOOF DETECTION FOR BIOMETRIC VALIDATION

(71) Applicant: Joshua Noel Hogan, Los Altos, CA (US)

(72) Inventor: Joshua Noel Hogan, Los Altos, CA (US)

( * ) Notice: Subject to any disclaimer, the term of this patent is extended or adjusted under 35 U.S.C. 154(b) by 64 days.

(21) Appl. No.: 16/185,781

(22) Filed: Nov. 9, 2018

(65) Prior Publication Data

US 2019/0138828 A1      May 9, 2019

Related U.S. Application Data

(60) Provisional application No. 62/584,029, filed on Nov. 9, 2017.

(51) Int. Cl.
| | | |
|---|---|---|
| *A61B 5/1172* | (2016.01) | |
| *G01B 9/02* | (2006.01) | |
| *G06F 21/32* | (2013.01) | |
| *A61B 5/00* | (2006.01) | |
| *G06K 9/00* | (2006.01) | |
| *A61B 5/145* | (2006.01) | |
| *G01N 21/17* | (2006.01) | |

(52) U.S. Cl.
CPC .......... *A61B 5/1172* (2013.01); *A61B 5/0066* (2013.01); *G01B 9/02091* (2013.01); *G06F 21/32* (2013.01); *G06K 9/00087* (2013.01); *A61B 5/14532* (2013.01); *G01B 2290/70* (2013.01); *G01N 2021/1787* (2013.01); *G06K 9/00114* (2013.01); *G06K 9/00906* (2013.01)

(58) Field of Classification Search
CPC . G01B 9/02091; A61B 5/0066; A61B 5/0073; A61B 3/102; G01N 21/4795; G01N 2021/1787; G06T 2207/10101; G06F 21/32; G06K 9/00087; G06K 9/00114; G06K 9/00906; G06K 9/0004; G06K 9/00288
See application file for complete search history.

(56) References Cited

U.S. PATENT DOCUMENTS

| | | | | |
|---|---|---|---|---|
| 7,982,879 B2* | 7/2011 | Desjardins | ......... | G01B 9/02043 356/477 |
| 9,115,972 B2* | 8/2015 | Hirose | ............... | G01B 9/02091 |
| 9,689,661 B2* | 6/2017 | Suter | ....................... | G02B 6/278 |
| 2013/0107272 A1* | 5/2013 | Hirose | ................. | A61B 5/0066 356/477 |
| 2013/0107277 A1* | 5/2013 | Hirose | .................. | A61B 3/102 356/512 |
| 2013/0155421 A1* | 6/2013 | Langstaff | ................. | G07D 7/12 356/630 |
| 2015/0369586 A1* | 12/2015 | Fukuhara | ........... | G01B 9/02058 356/479 |
| 2016/0063790 A1* | 3/2016 | Stewart | .................... | G07D 7/20 356/365 |
| 2016/0305762 A1* | 10/2016 | Suter | .................. | G01B 9/02011 |

(Continued)

*Primary Examiner* — Violeta A Prieto

(57) ABSTRACT

The invention provides an Optical Coherence Tomography (OCT) system capable of acquiring two orthogonally polarized depth scans from a target such as the fingerprint region of a finger. In the preferred embodiment the birefringence of tissue components and, optionally, other aspects of the target are measured in order determine a characteristic of the target, such as whether it is real of fake finger.

3 Claims, 4 Drawing Sheets

(56) References Cited

U.S. PATENT DOCUMENTS

| | | | | |
|---|---|---|---|---|
| 2017/0124408 A1* | 5/2017 | Hogan | ............... | G06K 9/00046 |
| 2018/0120084 A1* | 5/2018 | Osawa | ............... | G01B 9/02011 |
| 2018/0157924 A1* | 6/2018 | Hogan | ............... | G06K 9/00046 |
| 2019/0150799 A1* | 5/2019 | Hogan | ............... | G06K 9/00906 |

* cited by examiner

SPOOF DETECTION FOR BIOMETRIC VALIDATION

CROSS REFERENCES TO RELATED PATENTS OR APPLICATIONS

This US patent application, claims priority from provisional patent application 62/584,029 filed on 9 Nov. 2017. This US patent application is related to U.S. Pat. No. 9,721,138 titled "System and method for fingerprint validation, related to U.S. Pat. No. 7,526,329 titled Multiple Reference Non-invasive Analysis System, and U.S. Pat. No. 7,751,862 titled Frequency Resolved Imaging System, all three of which are incorporated by reference as if fully set down herein.

FIELD OF THE INVENTION

The invention described and illustrated in this application relates to the field of non-invasive imaging and analysis and measurement of targets such as tissue to image the tissue or to measure the concentration of analytes. In particular the invention relates to improving the performance of the non-invasive interferometric technologies such as Optical Coherence Tomography (OCT) for imaging and analyzing tissue including, but not limited to, skin tissue and retinal tissue. Such analysis includes using OCT to determine the concentration of analytes such as glucose in tissue or tissue fluids.

BACKGROUND OF THE INVENTION

The invention relates to non-invasive imaging and analysis techniques such as Optical Coherence Tomography (OCT). In particular it relates using optical interferometric techniques to monitor or measure surface and sub-surface attributes of human tissue to validate that the tissue being analyzed is living human tissue and is not synthetic or fake tissue. The invention may be used in conjunction with other surface imaging techniques. Validating that the tissue under analysis is not synthetic or fake is useful in secure identification, verification of life, authentication of identity, and other bio-metric applications.

Non-invasive imaging and analysis of targets is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process. In the case of quality control, it enables non-destructive imaging and analysis on a routine basis.

Optical coherence tomography (OCT) is a technology for non-invasive imaging and analysis. There are more than one OCT techniques. Time Domain OCT (TD-OCT) typically uses a broadband optical source with a short coherence length, such as a super-luminescent diode (SLD), to probe and analyze or image a target. Multiple Reference OCT (MRO) is a version of TD-OCT that uses multiple reference signals. Another OCT technique is Fourier Domain OCT (FD-OCT).

A version of Fourier Domain OCT, called Swept Source OCT (SS-OCT), typically uses a narrow band laser optical source whose frequency (or wavelength) is swept (or varied) over a broad wavelength range. In TD-OCT systems the bandwidth of the broadband optical source determines the depth resolution. In SS-OCT systems the wavelength range over which the optical source is swept determines the depth resolution.

Another version of Fourier Domain OCT, often referred to as Spectral Domain OCT (SD-OCT), typically uses a broad band optical source and a spectrometer to separate out wavelengths and detect signals at different wavelengths by means of a multi-segment detector.

OCT depth scans can provide useful sub-surface information including, but not limited to: sub-surface images of regions of tissue; measurement of thickness of layers of tissue; magnitude of regions of abnormal tissue growth; measurement of concentration of metabolites, such as glucose, in tissue fluids; measurement of concentration of metabolites, such as glucose, in blood. More generally OCT depth scans can provide useful sub-surface information regarding attributes of tissue.

The propagation of light through tissue and the scattering of light by tissue involve complex processes that alter the polarization state of light. Plane polarized light waves are light waves that vibrate in a single plane. A birefringent material causes the vibration plane of the light waves to rotate.

Human tissue in the fingerprint region at the tip of the finger is a complicated birefringent material. Different tissue layers have different degrees of birefringence, and, because tissue is so anisotropic, the amount of rotation within these layers varies. Those tissue layers having higher collagen content, such as the dermis, have higher birefringence. Thus, the propagation of polarized light through tissue undergoes complicated changes.

For example, as light propagates through tissue, the stratum corneum, the outer most layer of the epidermis, randomly rotates the state of polarization of light. As light continues through the tissue, it enters the papillary dermis layer where the polarization substantially remains in the arbitrary polarization state that was established in the stratum corneum. Upon reaching the deep dermis region (the reticular layer), the polarization state of light is further randomly rotated.

In addition to polarization modifying effects of real tissue, there are scattering coefficient related intensity variations in the in the light scattered from different layers, such as the epidermis and dermis. Furthermore speckle size and distribution in the separate layers have different characteristics.

It is often useful to acquire OCT sub-surface scans of tissue at known locations with respect to the tissue surface. While OCT can produce two dimensional images of the surface of a target such as tissue, there are conventional imaging technologies that can capture surface images, such as a camera employing a conventional charged coupled device (CCD). Such conventional imaging devices can readily capture images of the surface of tissue.

Tissue can be imaged to acquire a surface fingerprint by various techniques including, but not limited to: cameras using one or more conventional charged coupled device (CCD); an array of conducting sensors in conjunction with an RF generator (as in an iPhone fingerprint detector); ultrasonic imaging systems, such as those using capacitive micro-machined ultrasound transducers (CMUTs) or similar piezo based devices (PMUTs).

While existing fingerprint sensors, such as those using ultrasound techniques or those using an array of conducting sensors in conjunction with an RF generator, are used to ensure use by authorized individuals, such sensors are vulnerable to being hacked, for example, by artificial (stick on) fingerprints or fake fingers. Synthetic materials are being designed to more accurately mimic human tissue.

There is therefore an unmet need for a more reliable technique for distinguishing between real living human tissue and synthetic or fake tissue.

DETAILED DESCRIPTION OF A PREFERRED EMBODIMENT

Figure 1:
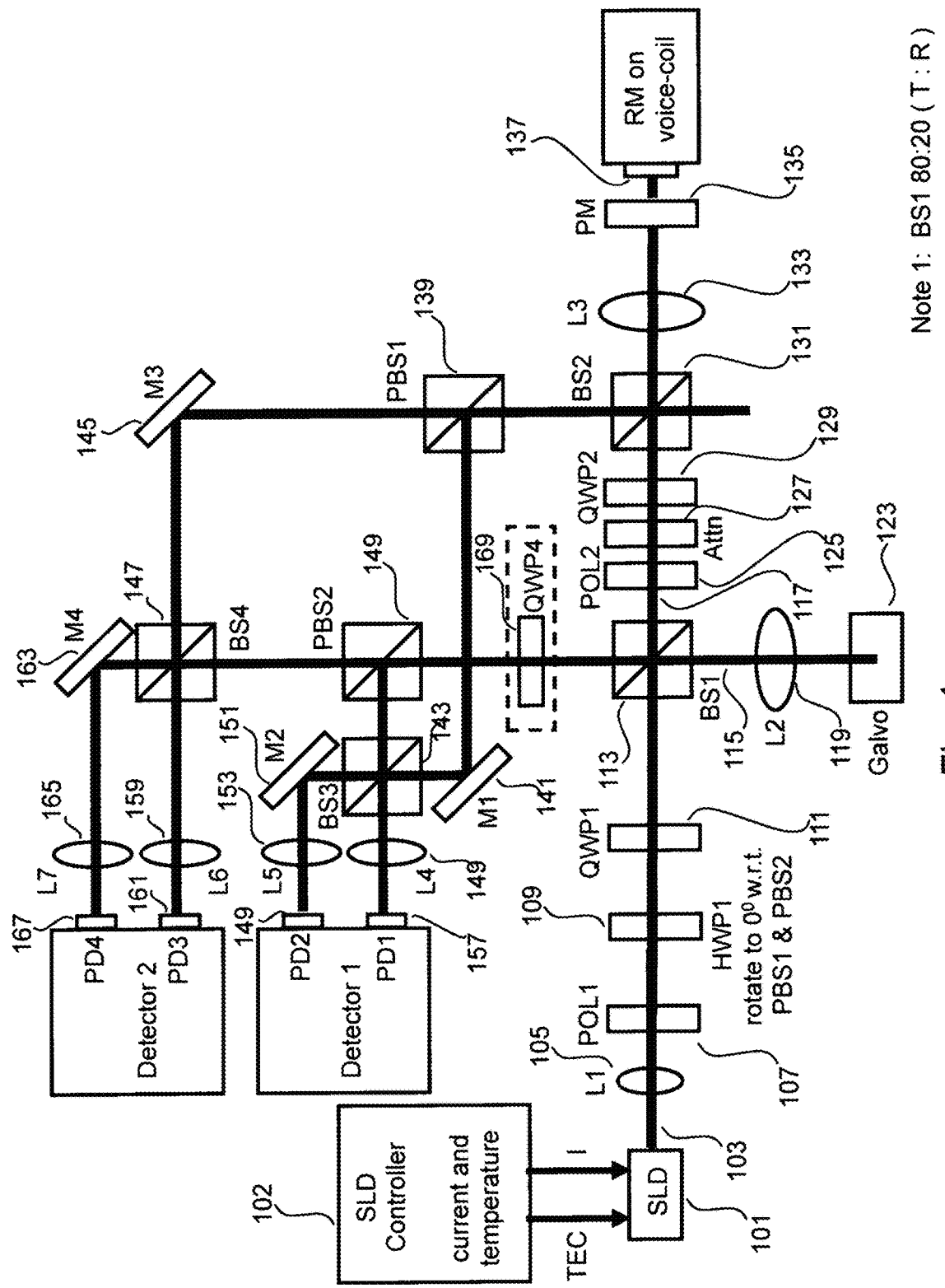
FIG. 1 of Sheet 1 depicts an MRO version of OCT capable of measuring two orthogonally polarized depth scans of a target.

In the preferred embodiment, depicted in FIG. 1 Sheet 1, an MRO version of OCT system capable of acquiring both polarization components of the light back-scattered from the tissue under analysis is used to acquire depth scans of the tissue to be analyzed.

In the preferred embodiment, circularly polarized light is applied to the target which consists of either real or synthetic (fake) tissue, however in other embodiments linearly polarized light is applied to the tissue. For purposes of this application "real" tissue refers to "real living" tissue.

The MRO system of FIG. 1 Sheet 1 has a broadband optical source such as a superluminescent diode (SLD) 101, controlled by an SLD controller 102 that emits light 103 at a center wavelength of approximately 1300 nm with a bandwidth of the order of 45 nm. The source is collimated by a lens (L1) 105 which outputs collimated infra-red light. The light passes through a polarizer (POL1) 107 where it is converted into a linearly polarized beam. It is transmitted through a half wave plate (HWP1) 109 and a quarter wave plate (QWP1) 111 that transforms the linearly polarized light beam into circularly polarized light, which is directed at an 80/20 non-polarized beam splitter (BS1) 113.

BS1 splits the light into a sample beam 115 and reference beam 117. BS1 being a non-polarized beam splitter for has the advantage of applying circularly polarized light to the tissue target. Furthermore, by choosing BS1 to transmit a higher proportion of light energy than is reflected (for example, 80% T and 20% R, or 80/20), a greater amount of the back-scattered light is transmitted to the detectors from the sample.

The sample beam 115 is then directed through a focusing lens (L2) 119 to a Galvo scanner 123 that directs the beam to a cylindrical lens (not shown) that provides the platen onto 121 which a finger to be analyzed is placed. The Galvo 123 performs 1D lateral scanning while the complete system, with the exception of the cylindrical platen, is translated in the orthogonal lateral direction to achieve 2D lateral scanning. Light back scattered from the tissue target returns to the Galvo 123, through L2 to BS1 where 80% is transmitted through to the detection system.

The reference path beam 117 passes through a second polarizer (POL2) 125, an attenuator (Attn) 127 and a second quarter wave plate (QWP2) 129 before being applied to a 50/50 non-polarizing beam splitter (BS2) 131. Note Attn 127 may be positioned before or after POL2 or QWP2. The light transmitted through BS2 passes through a focusing lens (L3) 133 to the partial mirror (PM) 135 in front of the reference mirror RM 137 on an oscillating voice coil. The multiple reflections between the RM and PM form the composite reference radiation that is the basis of generating multiple interference signals when combined with the light back scattered from the target. The light that is reflected at BS2 can be used to monitor the system light power as needed.

Upon reflection from the PM/RM, half of this composite reference light is directed by BS2 to a polarized beam splitter (PBS1) 139. The other half of the composite reference beam is eliminated by the QWP2 129, Attn 127 and POL2 125 combination thus eliminating light feedback and interference to the source and detection system. PBS1 139 splits the composite reference light into two orthogonal polarized beams. One of these components is reflected by the mirror (M1) 141 to the 50/50 non-polarizing beam splitter (BS3) 143, while the other component is reflected by the mirror (M3) 145 to the 50/50 non-polarizing beam splitter (BS4) 147.

The back-scattered sample signal collected by L2 119 is transmitted through BS1 113 to the polarized beam splitter (PBS2) 149, which splits the back-scattered sample light into two orthogonal polarized components. One of these polarization components of the back-scattered sample signal is reflected to BS3 143 where it is combined with a similarly polarized component of the composite reference signal to form two complementary interference signals. One of these interference signals is focused by a lens (L4) 149 onto a photo-detector (PD1) 157, while the second signal is re-directed by mirror (M2) 151 and focused by a lens (L5) 153 onto a photo-detector (PD2) 155. The combination of these sample and reference signals enable balanced detection of one component of the back-scattered light from the tissue.

The second polarization component of the back-scattered sample signal that is transmitted through PBS2 149 is combined with similarly polarized component of the composite reference signal at the 50/50 non-polarizing beam splitter (BS4) 147 to form two complementary interference signals. One signal is focused by a lens (L6) 159 onto a photo-detector (PD3) 161 while the second signal is re-directed by mirror (M4) 163 and focused by a lens (L7) 165 onto a photo-detector (PD4) 167. This combination of sample and reference signals yields balanced detection of the two orthogonal components of back-scattered light from the tissue.

The electronic signals output by PD1/PD2 in Detector 1 and PD3/PD4 in Detector 2 are combined in a balanced detection mode and applied to a trans-impedance amplifier prior to digitizing and digital signal processing.

In an alternative embodiment a quarter wave plate (QWP4) 169, shown with dashed lines surrounding it, is installed in the MRO system at the indicated location and changes the characteristics of the detected signal at each detector.

In both embodiments the differences between the signals from PD1/PD2 in Detector 1 and those of PD3/PD4 in Detector 2 are analyzed and used to determine the manner in which the two orthogonal polarization components differ from each other as a function of depth.

Figure 2:
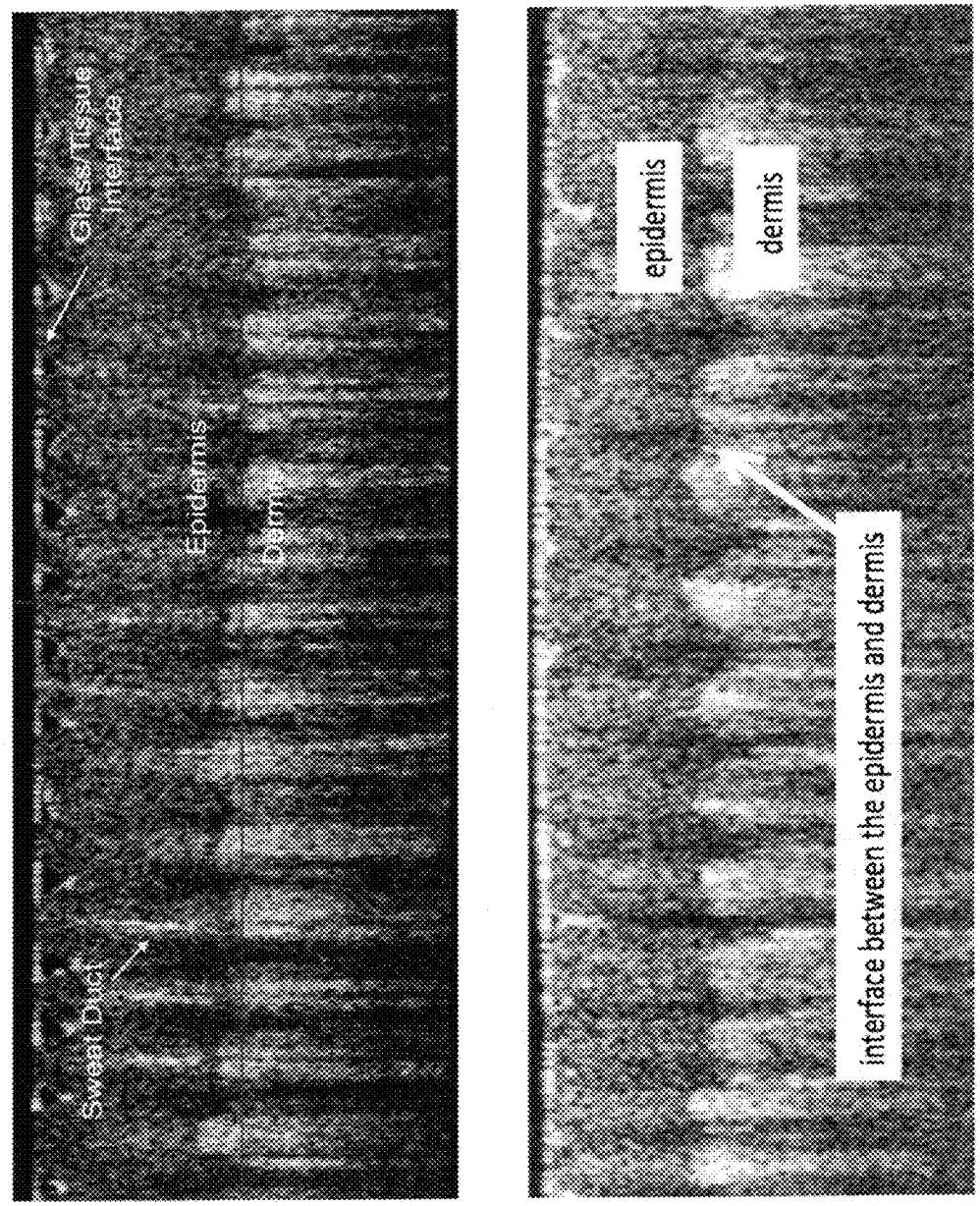
FIG. 2 of Sheet 2 depicts two examples of B-scans of tissue.

FIG. 2 Sheet 2 depicts two examples of a set of adjacent depth scans acquired by the MRO system displayed as images. The data sets comprising such images for the two orthogonal polarization components are processed, for example by subtraction, to determine differences between the two images and hence information about the birefringence of tissue as a function of depth.

In some embodiments the birefringence of specific layers of tissue is analyzed and compared with typical birefringence values of such specific layers to determine if the target under analysis is real tissue or fake tissue (i.e. a spoof).

In some embodiments the birefringence of specific interfaces of layers of tissue is analyzed and compared with typical birefringence values of such specific layer interfaces to determine if the target under analysis is real tissue or fake tissue (i.e. a spoof).

In some embodiments the change in birefringence, due to an environment change, of specific layers or interfaces of layers of tissue is analyzed and compared with typical birefringence values of such specific layers or layer interfaces to determine if the target under analysis is real tissue or fake tissue (i.e. a spoof).

In some embodiments an environment change includes, but is not limited to: a change in the pressure with which the finger to be analyzed is applied to a platen. In some embodiments an environment change includes, but is not limited to: a change in the temperature of the finger to be analyzed.

In some embodiments multiple adjacent B-scans are acquired to form a volume data set to be analyzed. In some embodiments a volume data set is acquired by employing lateral scanning techniques other than raster scans or stepped B-scans.

One or more B-scans or a volume scan are analyzed to determine consistency with either real tissue or synthetic tissue and thereby validate real tissue or detect a spoof comprised of fake synthetic or fake tissue.

Some embodiments verify that the level of birefringence of different layers is appropriate. Check if the average birefringence of different layers falls within a normal range for real tissue birefringence and determine a parameter or figure of merit that is a measure of the likelihood of there being a spoof layer present.

Some embodiments verify that the level of birefringence of different layer interfaces is appropriate. Check if the average birefringence of different layers interfaces fall within a normal range for real tissue birefringence and determine a parameter or figure of merit that is a measure of the likelihood of there being a spoof layer present.

In addition to or instead of analysis of birefringence to determine consistency with either real tissue or synthetic tissue, analysis of some or all of aspects described in the following embodiments may be included to determine a set of parameters or a set of figures of merit representative of actual living tissue. Note, the term appropriate is used in the following steps to mean consistent with typical attributes of real tissue i.e. that they do not deviate significantly from the range of values found in normal human tissue.

Some embodiments verify that the appropriate number of layers are present in the fingerprint B-scan image (epidermis, dermis, etc.) with an appropriate relationship and that their are no additional layers that would correspond to a fake layer. For example, automatically segment the B-scan image into the two most optimal layers (regardless of actually how many layers exist). Assume they are a superficial layer and a deep layer. Compute the average thickness of the superficial layer and check if the thickness is consistent with a normal epidermal thickness and thereby determine if there is a spoof layer present, or determine the likelihood of there being a spoof layer present.

Figure 3:
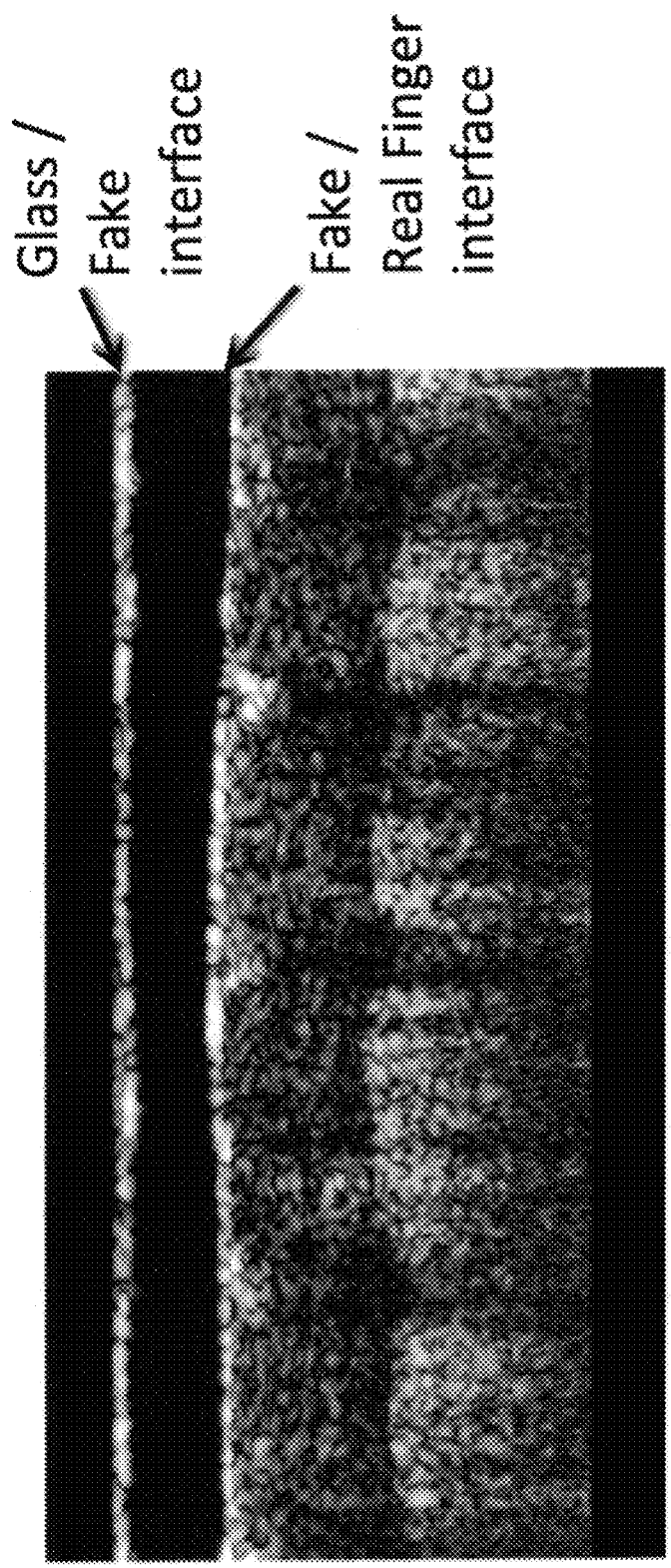
FIG. 3 of Sheet 3 depicts a B-scan of a fake fingerprint on the surface of a real finger.

Alternatively, or in addition, blindly re-segment both the superficial layer and the deep layer each into two more layers. Examine the new "superficial-superficial" boundary (located above the old superficial-deep boundary) and the new "deep-deep" boundary (located below the old superficial deep boundary). Ensure that these new, putative boundaries do not correspond to actual, extra boundaries between extra layers (i.e. spoof layers) by comparing the mean vertical gradient (averaged over transverse position) of the superficial-superficial and deep-deep boundaries to a threshold. Compute a figure of merit as a measure of the likelihood of there being a spoof layer present. Alternatively, or in addition, automatically segment the B-scan image into three layers and determine a parameter or figure of merit for the presence of three layer. The parameter or figure of merit is used as a measure of the likelihood of there being a spoof layer present. An example of a B-scan with an extra layer due to a transparent fake fingerprint is depicted in FIG. 3 Sheet 3.

Some embodiments verify that there are appropriate intensity variations within the epidermis and dermis layers, at their boundaries and that their relative intensities are appropriate. For example, compute the average intensity of the superficial layer and the average intensity of the deeper layer. Check if the average intensities fall within a normal range for tissue scattering. A layer that is either too optically clear or too optically dense may not represent tissue. The ratio of the average intensities of the superficial layer and the deep layer should also have a limited range in tissue. The average intensities and their ratio are used to determine a parameter or figure of merit that is a measure of the likelihood of there being a spoof layer present.

Some embodiments verify that the speckle size and distribution in the separate layers is appropriate. Compute the two-dimensional spatial Fourier transform of the speckle profile in the superficial layer, and the spatial Fourier transform of the speckle profile in the deep layer. Tissue will have a certain speckle size, which should appear as a well-defined peak on the two-dimensional spatial Fourier transform. Other scattering media (e.g. milk, glue, etc.) should have a characteristically different speckle size. Determine a parameter or figure of merit based on the spatial Fourier transform that is a measure of the likelihood of there being a spoof layer present.

Some embodiments verify that the dermal-epidermal junction has an appropriate contour. For example, compute the one-dimensional spatial Fourier transform of the boundary between the superficial and deep layers. This boundary should have "bumps" corresponding to rete ridges at a certain range of spatial frequencies. A flat boundary such as glass or plastic will not exhibit a characteristic spatial frequency. Determine a parameter or figure of merit based on the one-dimensional spatial Fourier transform that is a measure of the likelihood of there being a spoof layer present.

Some embodiments verify that the contour of the sub-dermal B-scan correlates appropriately with the surface B-scan or the corresponding line on a surface fingerprint. For example, compute the one-dimensional spatial Fourier transform of the boundary between the superficial and deep layers and compare this with a similar function at the same region of the surface fingerprint and determine a parameter or figure of merit based on the correlation between the two spatial Fourier transforms that is a measure of the likelihood of there being a spoof layer present.

Some embodiments generate a correlation map to determine temporal differences in tissue regions by comparing successively acquired co-located A-scans or closely adjacent A-scans or successively acquired co-located B-scans. The correlation mapping technique is described in the paper titled "Feasibility of correlation mapping optical coherence tomography (cmOCT) for anti-spoof sub-surface fingerprinting" (J. Biophotonics 1-5 (2013)/DOI 10.1002/jbio.20120000231), a technique typically used to identify blood flow.

Some embodiments (a) Compute correlation map. (b) Mark pixel locations that have a certain level of decorrelation. (c) Regardless of whether or not these pixel locations actually represent flow, compute both a depth-based and transverse-based histogram of decorrelation pixel locations. (d) Ensure that the histogram meets some pre-determined shape, such as (i) decorrelation pixels should be present in deep, but not superficial layer, (ii) decorrelation pixels should be clustered in superficial part of superficial layer, (iii) distribution of decorrelation pixels should not be uniform over depth, (iv) distribution of decorrelation pixels should not be uniform over transverse dimension. Determine a parameter or figure of merit based on one or more processed histograms that is a measure of the likelihood of there being a spoof layer present.

Some embodiments verify that the dynamic behavior of at least some of the above aspects behave in an appropriate manner when subjected to changing environmental factors, such as pressure. For example, measure the variation in layer thickness with pressure and check if the average variation with pressure falls within a normal range for real tissue and determine a figure of merit that is a measure of the likelihood of there being a spoof layer present. As another example, measure the variation in birefringence of one or more layers with pressure and check if the average variation with pressure falls within a normal range for real tissue and determine a parameter or figure of merit that is a measure of the likelihood of there being a spoof layer present.

In some embodiments, one or more parameters are used to define a closed boundary in n-dimensional space within which B-scans representative of actual, living fingerprints would be distinguished from B-scans of synthetic or fake fingerprints. Actual parameter ranges corresponding to actual, living fingerprints would be refined with the analysis of additional sets of real and spoof images.

In some embodiments, these parameters are used as input to a machine learning algorithm such as a "support vector machine" (SVM) in order to distinguish between real and synthetic or fake fingerprints.

In some embodiments, one or more figures of merit would be combined to determine the likelihood of there being a spoof layer present.

In some embodiments, these figures of merit are used as input to a machine learning algorithm such as a "support vector machine" (SVM) in order to distinguish between real and synthetic or fake fingerprints.

Many variations of a spoof detection or presentation detection attack system using some or all of the steps listed above are possible.

Figure 4:
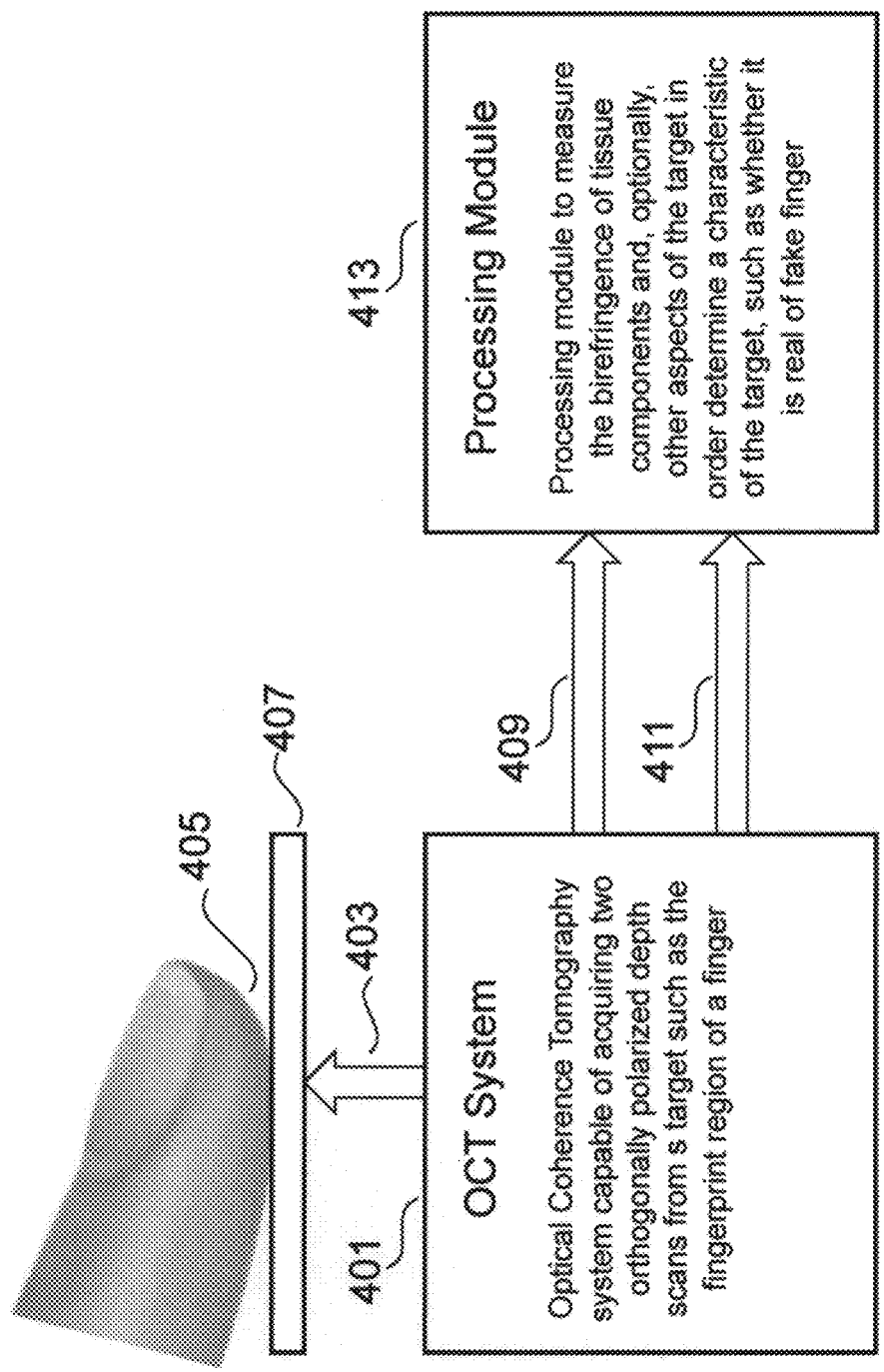
FIG. 4 of Sheet 4 depicts a preferred embodiment of the system.

The preferred embodiment is further illustrated in and described with respect to FIG. 4 of Sheet 4 where an Optical Coherence Tomography (OCT) system capable of simultaneously acquiring two orthogonally polarized depth scans from a target such as the fingerprint region of a finger is depicted.

The optical probe beam 403 is applied to the target to be analyzed, which in the preferred embodiment is the fingerprint area of a real or fake finger 405. The finger is depicted as resting on an optional platen 407 that is transparent to the probe beam.

The OCT system has a first and a second optical path for reference beams (described above in the discussion of FIG. 1 Sheet 1) that generate a first and second orthogonally polarized reference beams, wherein simultaneous interrogation of two orthogonally polarized components of probe beam back scattered from the target is enabled, such that a first orthogonally polarized depth scan of the target and a second orthogonally polarized depth scan of the target are generated.

A processing module 403 or processor receives first and second orthogonally polarized depth scans 409 and 411, and wherein the processor filters, digitizes and digitally processes the depth scans and determines the difference between said first and said second orthogonally polarized depth scans, and thereby provides a measure of the birefringence of the target or of components of the target and, optionally, other aspects of the target in order determine a characteristic of the target, such as whether it is real of fake finger.

Signals that comprise the two orthogonal depth scans 409 and 411 are connected to a processing module 413 where the signals 409 and 411 are filtered, digitized and digitally processed to measure the birefringence of tissue components and, optionally, other aspects of the target in order determine a characteristic of the target, such as whether it is real of fake finger.

In another preferred embodiment, an additional conventional imaging device (not shown) is used to acquire a surface image of the target to facilitate determining the identity of the fingerprint and to further assist in distinguishing between a real and fake finger.

In another preferred embodiment, additional strain gauges, or other pressure measuring devices, (not depicted) are embedded in the platen to determine the pressure being applied by the finger on the platen and thereby enable dynamic changes in birefringence to be measured.

In another preferred embodiment, the platen 407 can deform or be depressed proportional to the pressure being applied by the finger on the platen and thereby enable dynamic changes in birefringence to be measured. Since the location of the surface of the target platen responds to pressure of the target, such that change in location can be determined from a B-scan images (from the first and second orthogonally polarized depth scans) that includes the surface of the platen, thereby enabling changes in birefringence of said target due to change in pressure is measured.

Many variations of the OCT system used to detect the interference. While in the preferred embodiment an MRO system is the OCT system capable of detecting two orthogonal polarization components independently is depicted and described, in other embodiments other OCT systems could be used including, but not limited to, SS-OCT or FD-OCT or mode-locked OCT systems.

In the preferred embodiment, the characteristic of the target to be determined is whether it is a real finger of a fake finger. In other embodiments, the characteristic of the target to be determined is a different characteristic, such as the glucose concentration of a tissue component.

In embodiments where birefringence is not being measured, simpler MRO or OCT systems could be used.

In some embodiments, the parameter set or figures of merit set used to represent the tissue under analysis could be weighted by one or more known attributes of the subject whose identity the fingerprint purported to correspond to. Such attributes include, but are not limited to, gender, race, age, physical weight and size, medical conditions, such as diabetes.

The (weighted or un-weighted) parameter set or figures of merit set derived by analyzing one or more B-scans or a volume scan of the tissue under analysis is processed by an algorithm that distinguishes a parameter set or figures of merit set of actual, living fingerprints from that of synthetic or fake tissue.

Such a distinguishing algorithm may be a machine learning algorithm or an algorithm derived from systematic analysis of the characteristics of real tissue and of synthetic or fake tissue.

Many variations of the above embodiments are possible. The scope of this invention should be determined with reference to the description and the drawings along with the full scope of equivalents as applied thereto.

What is claimed is:

1. An optical coherence tomography system, said system capable of simultaneously acquiring two orthogonally polarized depth scans from a target, said system comprising:
   an optical coherence tomography system;
   a first and a second optical path for reference beams that generate a first and second orthogonally polarized reference beams, wherein simultaneous interrogation of two orthogonally polarized components of probe beam back scattered from said target is enabled, such that a first orthogonally polarized depth scan of said target and a second orthogonally polarized depth scan of said target are generated;
   a processor, wherein said processor receives said first and said second orthogonally polarized depth scans, and wherein said processor determines the difference between said first and said second orthogonally polarized depth scans, and thereby providing a measure of the birefringence of said target, and determines if said target is fake.

2. The system of claim 1, further including a target platen, and a pressure measuring device in said target platen, such that change in birefringence of said target due to change in pressure is measured, using information from said first and said second orthogonally polarized depth scans.

3. The system of claim 1, further including a target platen that responds to pressure of the target, such that change in birefringence of said target due to change in pressure is measured, using information from said first and said second orthogonally polarized depth scans.

* * * * *